United States Patent [19]

Bojovich

[11] Patent Number: 4,949,709
[45] Date of Patent: Aug. 21, 1990

[54] COMBINATION TOOTHBRUSH AND WATER DEFLECTOR APPARATUS

[76] Inventor: Momcilo Bojovich, Fregattv 16II, Lidingo, Sweden, 18137

[21] Appl. No.: 381,475

[22] Filed: Jul. 18, 1989

[51] Int. Cl.$^5$ ............................................. A61H 9/00
[52] U.S. Cl. ................................... 128/66; 15/167.1
[58] Field of Search .............. 128/66, 62 A; 15/167.1, 15/167.2; 132/308, 309, 310, 311; D4/108

[56] References Cited

U.S. PATENT DOCUMENTS

| | | | |
|---|---|---|---|
| D. 53,453 | 6/1919 | Lloyd | D4/108 |
| D. 95,777 | 5/1935 | Peterkin et al. | D4/108 |
| D. 201,350 | 6/1965 | Taylor | D4/108 |
| D. 221,828 | 9/1971 | Yamada | D4/108 |
| 851,550 | 4/1907 | Nerius | 15/167.1 |
| 2,028,519 | 1/1936 | Peterkin et al. | 15/167.1 |
| 2,083,217 | 6/1937 | Brothers et al. | 15/167.1 |
| 2,154,209 | 4/1939 | Kohn | 15/167.1 |
| 2,468,298 | 4/1949 | Kahn | D4/108 |

FOREIGN PATENT DOCUMENTS 2315238  1/1977  France ............................... 15/167.1

Primary Examiner—John J. Wilson
Attorney, Agent, or Firm—Leon Gilden

[57] ABSTRACT

A toothbrush and water deflector is set forth wherein a toothbrush provided with an elongate handle defining an upper surface and a lower surface includes a matrix of bristles extending orthogonally relative to a bottom surface of the handle at a first terminal end thereof with a water deflector apparatus for use in combination with a water faucet at an upper surface of the handle. The water deflector organization includes a first, discontinuous annular rim defining a keyhole opening overlying a base annular surface spaced below and parallel to the annular rim with an outlet defined between the annular rim and the annular surface whereupon positioning of the water deflector apparatus adjacent a water faucet will direct water towards a user of the organization.

2 Claims, 1 Drawing Sheet

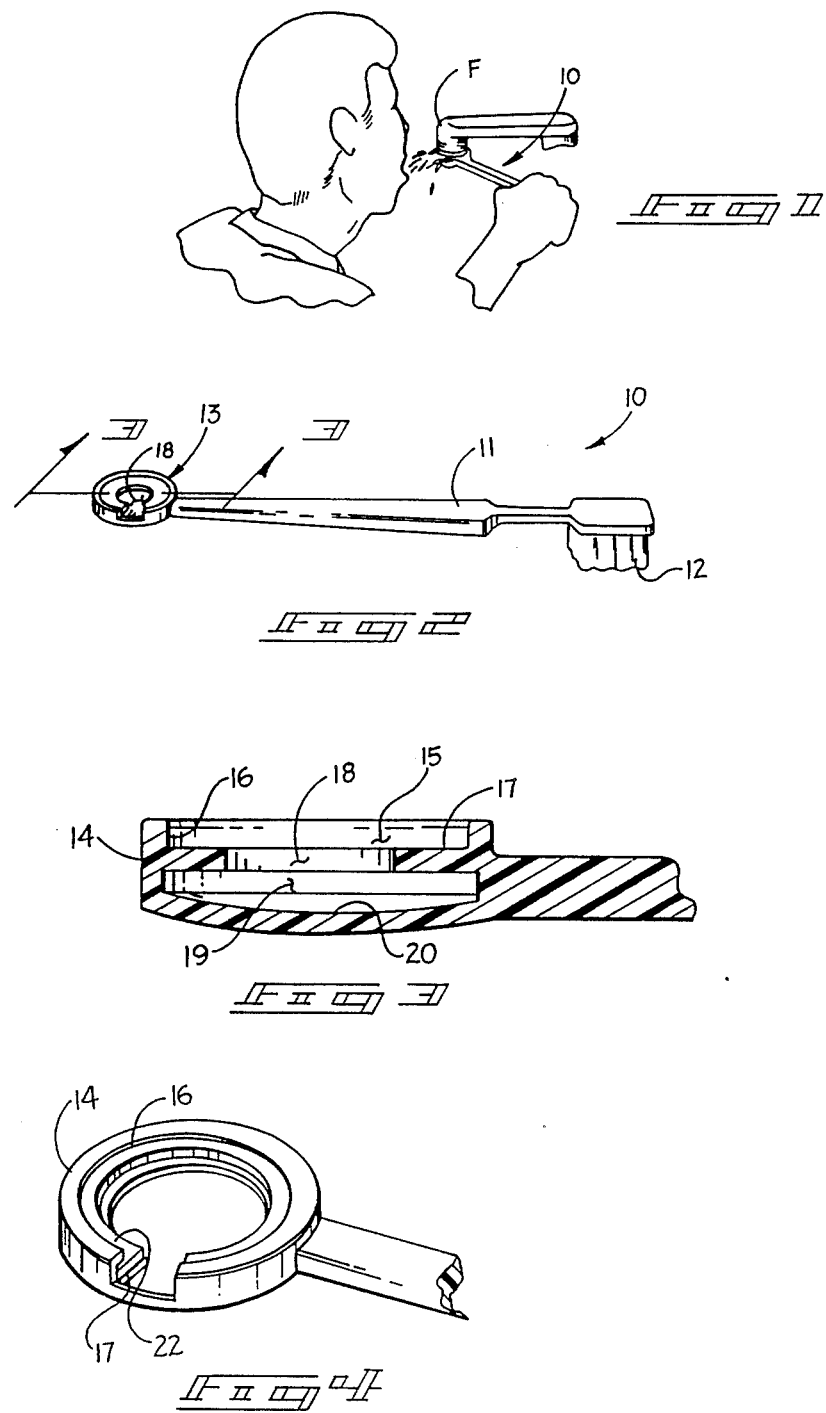

COMBINATION TOOTHBRUSH AND WATER DEFLECTOR APPARATUS

BACKGROUND OF THE INVENTION

1. Field of the Invention

The field of invention relates to toothbrush organizations, and more particularly pertains to a new and improved combination toothbrush and water deflector apparatus wherein the same utilizes a conventional toothbrush in combination with a water deflector apparatus for use in combination with a water faucet to direct a stream of water towards an individual subsequent to a bushing procedure.

2. Description of the Prior Art

The prior art has utilized toothbrushes and combinations of such brushes to enhance the convenience of their use. Typically subsequent to a toothbrush and procedure, an individual needs to flush the mouth region with fresh water for a rinsing procedure. Commonly, an appropriate receptacle is not conveniently available to effect such procedure with an individual attempting to obtain water from an associated faucet by various awkward and, at times, non-hygienic procedure. To overcome the shortcomings of such a procedure, the instant invention sets forth an organization not set forth by the prior art to provide a means of directing a stream of water towards an individual subsequent to a toothbrushing operation. Examples of the prior art may be found in U.S. patents typified by U.S. Pat. No. 2,468,298 to Kahn wherein a toothbrush is provided in combination with a dental floss support apparatus for a flossing operation prior to toothbrushing procedures.

The Design U.S. Pat. Nos. 221,828 to Yamada, et al., 53,453 to Lloyd, 201,350 to Taylor, and 95,777 to Peterkin set forth various toothbrushes in combination with items such as cups, spoons and the like that an individual may utilize in an attempt to convey water from an appropriate water source to an individual.

As such, it may be appreciated that there is a continuing need for a new and improved combination toothbrush and deflector apparatus wherein the same addresses both the problems of ease of use and effectiveness in construction, and in this respect, the present invention substantially fulfills this need.

SUMMARY OF THE INVENTION

In view of the foregoing disadvantages inherent in the known types of toothbrush apparatus now present in the prior art, the present invention provides a combined water deflector and toothbrush apparatus wherein the same provides a means of directing a flow of water from an associated faucet to a user for rinsing subsequent to a toothbrushing procedure. As such, the general purpose of the present invention, which will be described subsequently in greater detail, is to provide a new and improved combined water deflector and toothbrush apparatus which has all the advantages of the prior art toothbrush apparatus and none of the disadvantages.

To attain this, the present invention includes a toothbrush provided with an elongate handle formed with upper and lower overlying surfaces with a matrix of toothbrush bristles directed orthogonally outwardly of a bottom surface of the handle proximate a first end of the handle with a water deflector arrangement arranged at a second end of the handle. The deflector apparatus includes a cylindrical housing diametrically aligned and integrally secured to the second end of the handle with an annular discontinuous wall with an annular rim integrally secured to the wall wherein the rim is a further discontinuous annular arrangement with the discontinuous wall and the discontinuous rim forming a gap by alignment of their discontinuities with the discontinuities ranging from an angle of twenty to forty degrees. The discontinuous rim overlies a lower chamber wherein a water faucet is positioned in engagement with the rim and directs a flow of water through a central aperture of the rim into the lower chamber and from the lower chamber directs the water exteriorly of the apparatus through the gap formed within the annular wall of the cylindrical housing.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved combined water deflector and toothbrush apparatus which has all the advantages of the prior art toothbrush apparatus and none of the disadvantages.

It is another object of the present invention to provide a new and improved combined water deflector and toothbrush apparatus which may be easily and efficiently manufactured and marketed.

It is a further object of the present invention to provide a new and improved combined water deflector and toothbrush apparatus which is of a durable and reliable construction.

An even further object of the present invention is to provide a new and improved combined water deflector and toothbrush apparatus which is susceptible of a low cost of manufacture with regard to both materials and labor, and which accordingly is then susceptible of low prices of sale to the consuming public, thereby making such combined water deflector and toothbrush apparatus economically available to the buying public.

Still yet another object of the present invention is to provide a new and improved combined water deflector and toothbrush apparatus which provides in the apparatuses and methods of the prior art some of the advantages thereof, while simultaneously overcoming some of the disadvantages normally associated therewith.

Still another object of the present invention is to provide a new and improved combined water deflector and toothbrush apparatus wherein the same provides a discharge organization in combination with a sealing arrangement for a faucet to direct a flow of water from the faucet to a user of the toothbrush.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustation of the instant invention in use with a conventional water faucet.

FIG. 2 is an isometric illustration of the instant invention.

FIG. 3 is an orhtographic view taken along the lines 3—3 of FIG. 2 in the direction indicated by the arrows.

FIG. 4 is an isometric illustration of a modified sealing arrangement utilized by the instant invention.

DESCRIPTION OF THE PREFERRED EMBODIMENT

With reference now to the drawings, and in particular of FIGS. 1 to 4 thereof, a new and improved combined water deflector and toothbrush apparatus embodying the principles and concepts of the present invention and generally designated by the reference numeral 10 will be described.

More specifically, the combined water deflector and toothbrush apparatus 10 essentially comprises an elongate handle 11 formed with an upper surface overlying a lower surface coextensively therewith with a matrix of toothbrush bristles 12 extending outwardly orthogonally adjacent a first terminal end of the elongate handle 11 extending from a bottom surface thereof. Integrally secured to a second end of the handle 11 is the water deflector apparatus 13. The deflector apparatus 13 is formed with a cylindrical housing 14 diametrically aligned with the handle 11 with a discharge outlet 21 arranged orthogonally relative to the elongate handle 11.

The cylindrical housing 14 includes an upper annular recess 15 extending downwardly from the annular wall 16 defining the cylindrical housing 14. The annular wall 16 is formed as a discontinuous annular wall with an opening defined by a gap of twenty to forty degrees. Integrally secured to and extending orthogonally interiorly of the annular wall 16 is a discontinuous planar annular rim 17, also formed with an annular discontinuity of twenty to forty degrees. It is noted that the discontinuity of the annular wall 16 and the annular rim 17 are aligned with one another to define the discharge outlet 21. The annular rim 17 is formed with an angular central aperture 18 coaxially arranged relative to the cylindrical housing 14 and provides entrance to a chamber 19 defined by the overlying annular rim 17 and an underlying convex bottom wall 20. The annular rim 17 is of a diameter less than that of a faucet "F" which is positionable in sealing arrangement with an upper surface of the annular rim 17 to direct water from the faucet "F" through the annular aperture 18 and into the chamber 19 and from there, directed through the discharge outlet 21 to a user of the apparatus. Further, the wall 16 is of a diamether greater than that of the faucet "F" to receive the faucet "F" wholly upon an upper surface of the annular rim 17.

Reference of FIG. 4 illustrates the annular rim 17 formed with a resilent planar seal coextensively arranged and laminated onto an upper surface of the angular rim to enhance a sealing between the discharge opening of a faucet "F" and the annular rim 17.

As to the manner of usage and operation of the instant invention, the same should be apparent from the above disclosure, and accordingly no further discussion relative to the usage and operation of the instant invention shall not provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A combination water deflector and toothbrush apparatus for use with a water faucet defined by a discharge nozzle of a predetermined diameter, said apparatus comprising, an elongate handle defined by an upper surface coextensive with and overlying a bottom surface, and a matrix of toothbrush bristles extending outwardly of the bottom surface adjacent a first end of the handle, and a water deflector means for directing water from the faucet through a discharge outlet formed in the water deflector means wherein the water deflector means is integrally secured to a second end of the handle, and wherein the water deflector means is defined by a cylindrical housing integrally secured to the second end of the handle along a diameter of the cylindrical housing, and the discharge outlet is arranged orthogonally through a discontinuous wall of the cylindrical housing orthogonally relative to the elongate handle, and wherein the discontinuous wall is annular and defines an opening between twenty and forty degrees of arc through the wall, and wherein an angular rim is disposed and integrally secured below an upper terminal edge of the annular wall and integrally secured to the annular wall interiorly thereof, and the angular rim is of a planar configuration and defines an annular rim discontinuity and arranged between twenty and forty degrees of arc aligned with the discontinuity of the annular wall, and wherein the annular rim includes a central aperture therethrough, and the annular rim overlies a chamber defined between the annular rim and an underlying concave floor, and the aperture is of a diameter less than that of the predetermined diameter, and the annular wall is of a diameter greater than the predetermined diameter.

2. A combination water deflector and toothbrush apparatus as set forth in claim 1 wherein the annular rim further includes a resilient seal with a planar upper surface laminated to an upper surface of the annular rim to enhance a sealing between the faucet and the annular rim.

* * * * *